(12) United States Patent
Knott et al.

(10) Patent No.: US 9,078,935 B2
(45) Date of Patent: Jul. 14, 2015

(54) APPARATUS AND METHOD OF STERILIZING CONTAINERS WITH A CHARGE CARRIER SOURCE INTRODUCED INTO THE CONTAINERS

(71) Applicant: KRONES AG, Neutraubling (DE)

(72) Inventors: Josef Knott, Neutraubling (DE); Patrick Engelhard, Neutraubling (DE); Hans Scheuren, Neutraubling (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 13/625,864

(22) Filed: Sep. 24, 2012

(65) Prior Publication Data
US 2013/0084211 A1 Apr. 4, 2013

(30) Foreign Application Priority Data
Sep. 30, 2011 (DE) .......................... 10 2011 054 097

(51) Int. Cl.
*A61L 2/08* (2006.01)

(52) U.S. Cl.
CPC ............. *A61L 2/087* (2013.01); *A61L 2202/23* (2013.01); *H01J 2237/162* (2013.01); *H01J 2237/31* (2013.01)

(58) Field of Classification Search
CPC ........................................................ A61L 2/08
USPC ........................................................ 422/22
See application file for complete search history.

(56) References Cited

U.S. PATENT DOCUMENTS

| 3,163,793 | A | * | 12/1964 | Borman ........................ 315/363 |
| 6,139,796 | A | * | 10/2000 | Kristiansson et al. .......... 422/22 |
| 7,145,155 | B2 | * | 12/2006 | Nablo et al. ............... 250/492.1 |
| 7,520,108 | B2 | | 4/2009 | Kristiansson et al. .......... 53/426 |
| 7,759,661 | B2 | * | 7/2010 | Avnery ...................... 250/493.1 |
| 2008/0136064 | A1 | * | 6/2008 | MacDonald et al. .......... 264/478 |
| 2009/0045350 | A1 | * | 2/2009 | Humele et al. ........... 250/455.11 |
| 2010/0054987 | A1 | | 3/2010 | Krueger et al. .................... 422/3 |
| 2011/0012032 | A1 | | 1/2011 | Bufano et al. ............. 250/492.3 |
| 2011/0016829 | A1 | | 1/2011 | Drenguis et al. ................ 53/426 |
| 2011/0084221 | A1 | | 4/2011 | Eguchi et al. .............. 250/492.3 |
| 2012/0294758 | A1 | | 11/2012 | Avnery ............................ 422/1 |

FOREIGN PATENT DOCUMENTS

| CN | 101416255 | 4/2009 | ............... G21K 5/04 |
| DE | 102009008633 | 8/2010 | ............... A61L 2/08 |
| EP | 2161202 | 3/2010 | ............... A61L 2/08 |
| JP | 2001-225814 A | * 8/2001 | |

(Continued)

OTHER PUBLICATIONS

English language machine translation of JP 2001-225814A, published Aug. 21, 2001; inventor: Matsuki.*

(Continued)

*Primary Examiner* — Sean E Conley
(74) *Attorney, Agent, or Firm* — Hayes Soloway P.C.

(57) ABSTRACT

A method of sterilizing containers, and in particular of plastics material containers is disclosed, wherein an inner wall of the containers is sterilized by being acted upon with charge carriers. A sterilization device which includes a charge generation device is introduced into the container (10) through an opening in the container and generates the charge carriers in the interior of the container.

26 Claims, 2 Drawing Sheets

(56) References Cited

FOREIGN PATENT DOCUMENTS

| WO | WO9707024 | 2/1997 | ............. B65B 55/04 |
|----|-----------|--------|--------------------------|
| WO | WO2009/095182 | 6/2009 | ................ A61L 2/08 |

OTHER PUBLICATIONS

German Search Report for application No. 10 2011 054 097.0, dated Aug. 3, 2012 (5 pgs).

English translation of First Office Action issued is corresponding Chinese Patent Appln. No. 201210372318.3 dated Apr. 25, 2014 (2 pgs).

Search Report issued in corresponding Appln. No. 12184121.7-1356, dated Mar. 15, 2013—no translation—(9 pgs).

* cited by examiner

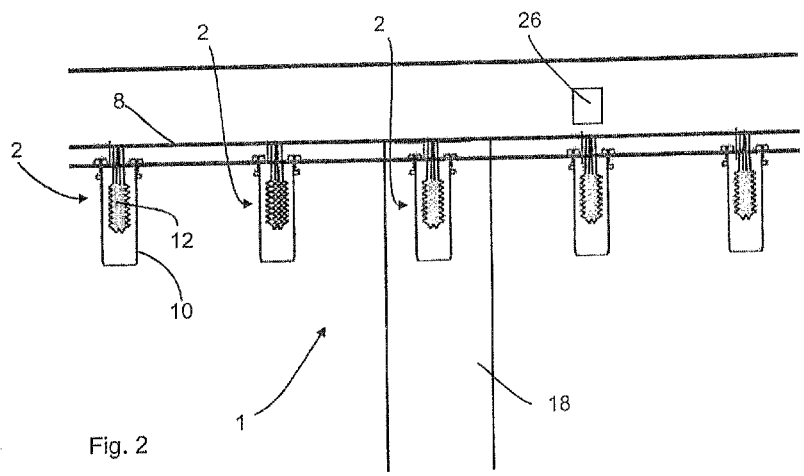
Fig. 2
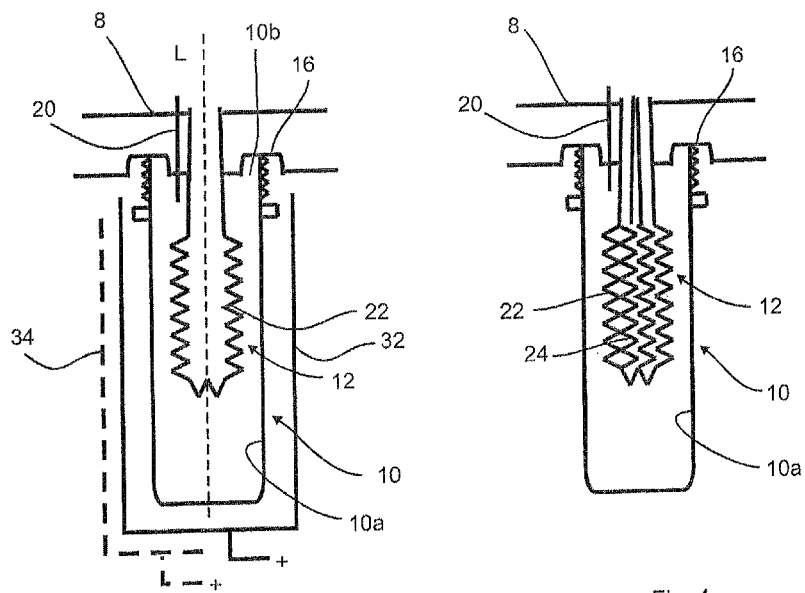
Fig. 3
Fig. 4

APPARATUS AND METHOD OF STERILIZING CONTAINERS WITH A CHARGE CARRIER SOURCE INTRODUCED INTO THE CONTAINERS

FIELD OF THE INVENTION

The present invention relates to a method and an apparatus for the sterilization of containers, and in particular of plastics material containers.

BACKGROUND OF THE INVENTION

The sterilization of a container to be filled is, as well as the actual filling procedure, an essential process step, in particular in an aseptic filling plant. The possible forms of sterilization vary with respect to the disinfection agents and the performance of the process. What is common to them all, however, is the fact that the destroying action is carried out on the basis of chemical processes. More recent developments known from the prior art differ from these and make use of ionizing radiation in order to achieve a reduction in the germs. In the majority of applications this radiation comprises accelerated charge carriers and, in particular, accelerated electrons which are produced in a corresponding plant and are introduced into the container to be sterilized. The advantage of this procedure consists in the reduction or avoidance of the use of chemical substances. Nevertheless these apparatus, however, have acceleration plants which are in part not yet established and, as a result, are expensive and, in addition, they have a relatively complicated circuitry and monitoring. In addition, on account of the stray radiation which occurs a screen has to be present around the entire plant or around individual parts of this plant.

An apparatus for the sterilization of containers is known from DE 10 2009 008633 A1. In this case the containers are conveyed along a pre-set conveying path, more precisely through a treatment room. Here sterilization is carried out by acting upon the containers with electrons, a sterilization device of this type having a generating device for generating the electrons, as well as an accelerating device in order to accelerate the electrons generated by the generating device in the direction of the containers present in the treatment room. In this case a gas pressure inside the treatment room is below the gas pressure outside the treatment room. It is therefore suggested that the electrons should be accelerated in a region which is under a relatively low pressure in order to increase the reach of these electrons in this way.

The present systems which are available on the market and which are used for the sterilization have an electron generation apparatus and a grouping and mechanical solutions to the transmission of the electron beam into the container to be sterilized. Expressed more precisely, in the case of these plants a beam finger is usually introduced into the containers and the electrons are accelerated through this beam finger in the direction of an outlet window and they then issue out of the outlet window and onto the inner wall of the containers. In order to ensure the effect and transmission of the beam, the electrons generally have to be accelerated to a high degree. The acceleration voltage required for this amounts to up to 150 kV. The kinetic energy of the electrons is increased accordingly and undesired radioactive or X-ray radiation is produced to the same degree.

A further drawback of previous plants and apparatuses for the generation of electron beams is the problem of conveying the electrons from the generator source to the site of operation. The molecules present in the interspace, which occur in the air or in the existing outlet window, obstruct the reach of electron beams to a significant degree. As a consequence the acceleration of the electrons has to be adapted, this being a step which in turn will increase the size, the complexity, the risk potential and the screening, as well as the costs of the plant as a whole.

The object of the present invention is therefore to make available a method and an apparatus which avoid the use of very high acceleration voltages. In addition, the costs of a plant of this type for the sterilization of containers should be reduced as a whole.

SUMMARY OF THE INVENTION

In the case of a method according to the invention for the sterilization of containers, and in particular of plastics material containers, an inner wall of these containers is sterilized by being acted upon with charge carriers, and in particular with electrons. To this end a sterilization device is introduced into the container—in particular through an opening and preferably an mouth in this container. This sterilization device has a charge carrier generation device.

According to the invention the charge carrier generation means is introduced into the container at least in part and generates the charge carriers in the interior of the container.

Whereas in the prior art the charge carriers or electrons are generated outside the container and are accelerated only into the container, it is new proposed that the generation or electrons itself should be moved into the container to be sterilized. The charge carriers are thus now generated only inside the container. In this way, it is possible to dispense with the provision of very high acceleration voltages for accelerating the electrons. Between the electron generation device and the inner wall of the container it is usual for only very short distances to have to be covered, so that a high acceleration of the electrons is not necessary.

In the case of a further preferred method the charge carrier generation device is introduced into the container in a longitudinal direction of the latter. It is advantageous for the containers to be moved during the sterilization itself—in particular in a direction which is different from the insertion direction of the charge carrier generation device into the containers. As mentioned above, the charge carriers are in particular electrons.

In the case of a further advantageous method an underpressure (with respect to an atmospheric pressure) is generated inside the container at least for a time before or during the sterilization procedure. It is thus possible, for example, for an electron cloud to be generated inside the container in a rough or fine vacuum which in turn is present in the container to be sterilized. In this way, it is possible for the electrons to be conveyed virtually spontaneously to the corresponding operating surface. Because of the absence of interfering molecules, the energy required for this can be applied in an approximate manner and advantageously even without further acceleration voltage. The electrons deactivate cell compartments and molecules of the undesired micro-organisms by ionization on the surface to be sterilized.

In the case of a further advantageous method a pressure, which is between 0.0005 mbar and 800 mbar, preferably between 0.0005 mbar and 600 mbar, preferably between 0.001 mbar and 300 mbar, and in a particularly preferred manner between 0.001 mbar and 100 mbar, is generated in the interior of the container. With these pressure ratios the electrons have a relatively wide reach, so that, as mentioned, it is possible to dispense with additional acceleration voltages and in any case with very high acceleration voltages. The acceleration voltages, if used, are advantageously below 100 kV, preferably below 50 kV, and preferably below 10 kV.

It is advantageous if the container to be sterilized is a plastics material pre-form. For numerous reasons, plastics material pre-forms of this type are particularly suitable for the sterilization carried out here. On the one hand, they usually have a cylindrical main body, so that the distance between the electron generation device and the inner wall of the plastics material pre-form remains substantially constant along the longitudinal direction of the plastics material pre-forms. In addition, the plastics material pre-forms also have a very high degree of stability and can therefore be acted upon with an under-pressure. In the case of other containers an under-pressure of this type could even lead to deformation or implosion of the container.

It would also be possible for the containers to be turned, in particular about a longitudinal axis, with respect to the charge carrier generation device during the sterilization procedure or during the activation of the aforesaid charge carrier generation device. In this way, a uniform irradiation of the inner wall of the containers can be provided even if the electrons are not discharged uniformly in the peripheral direction. It would then also be possible for the electrons now to be accelerated in a preferred direction starting from the generation device. It is preferable in this case for the containers to be turned, but it would also be possible for the charge carrier generation device situated inside the containers to be turned about the preferred longitudinal axis.

In the case of a further advantageous embodiment the containers are conveyed along a pre-set conveying path during their sterilization. It is advantageous for this to be a circular conveying path.

In the case of a further advantageous embodiment the plastics material pre-forms are held on a holding device by an under-pressure. It is therefore proposed that the plastics material pre-forms should be transferred to a holding device, should then be acted upon with an under-pressure, and should also be held on this holding device by this under-pressure.

In this context it should be noted that an under-pressure of this type can optionally also be produced in glass containers, so that these too are also possibly suitable for the sterilization described here.

The present invention further relates to an apparatus for the sterilization of containers, and in particular of plastics material containers. This apparatus has a sterilization device which acts upon an inner wall of the plastics material containers with charge carriers. In this case the sterilization device has a charge carrier generation device which generates the charge carriers.

According to the invention the charge carrier generation device is designed in such a way that it is capable of being introduced into the interior of the container.

In contrast to the prior art it is thus also proposed with respect to the method that the charge carrier generation device itself should be introduced into the container (and not for example an outlet window, by way of which highly accelerated electrons can be discharged). It is advantageous for the charge carrier generation device to be capable of being introduced into the container through an mouth in the latter. In contrast to the prior art it is thus advantageous for no outlet window to be introduced into the containers, but the generation device itself.

In the case of a further advantageous embodiment the apparatus has a conveying device which conveys the containers at least for a time during their sterilization. In addition, the apparatus also has a movement device which introduces the sterilization or applying device into the container. In this case it is possible for the charge carrier generation device to be moved in a longitudinal direction of the container, but it is advantageous for the charge carrier generation device to remain fixed in this longitudinal direction and for the container to be moved with respect to it.

In the case of an advantageous embodiment the apparatus has a rotatable carrier on which a plurality of sterilization devices are arranged. In the case of a further advantageous embodiment the apparatus has a pressure application device which acts upon the containers with an under-pressure. In particular, also as a result of the use of this under-pressure, the reach of the electrons in the interior of the containers can be increased. It would also be possible in many cases, however, for even a certain sterilization to be possible without the generation of an under-pressure. In addition, it would also be possible for not only the containers themselves to be acted upon with the under-pressure, but [also] the space in which the containers are conveyed. It is advantageous, however, for only the interiors of the containers to be acted upon with the aforesaid under-pressure. In the case of a further advantageous embodiment the apparatus has a deflecting device which directs the charge carriers in the direction of the inner wall of the containers. In this way for example, a positive electrode could be provided outside the plastics material containers and surrounding these plastics material containers.

In this way for example, a hot cathode could be introduced into the interior of the containers. In this case if would also be possible for this hot cathode to be introduced without a glass flash surrounding it and for the necessary vacuum to be generated in the container itself. In the case of an advantageous embodiment the radiation generation device has a first electrical conductor which is capable of being introduced into the container and of having a current flow through it. As known per se from the prior art, the electrons are released by the aforesaid current flow. This can be a tungsten cathode for example.

In the case of a further advantageous embodiment the radiation generation device can have a second electrical conductor which is capable of being introduced into the container and of having a current flow through it. This second conductor can advantageously be connected in this case parallel to the first conductor. In this case the design can be such that the second conductor is activated in the event of failure of the above-mentioned first conductor capable of having a current flow through it, so that even in the event of failure of an electrical conductor the sterilization can be continued.

The present invention further relates to a plant for the treatment of plastics material containers. According to the invention this plant has an apparatus of the type defined above. It is advantageous for the plant also to have an apparatus for shaping plastics material pre-forms into plastics material containers. In the case of a further advantageous embodiment the apparatus mentioned above is arranged in front or the apparatus for shaping plastics material pre-forms into plastics material containers in the conveying direction of the plastics material containers. In the case of a further advantageous embodiment the plant also has a heating device for heating plastics material pre-forms and in this case this heating device is arranged in front of the apparatus for shaping plastics material pre-forms into plastics material containers in the conveying direction of the plastics material pre-forms.

The apparatus according to the invention can be arranged in this case between the heating device and the apparatus for shaping plastics material pre-forms into plastics material containers in the conveying direction of the plastics material pre-forms. It is advantageous, however, for the apparatus according to the invention to be arranged in front of the heating device for heating plastics material pre-forms, for example in front of or in an inlet region of this heating device.

BRIEF DESCRIPTION OF THE DRAWINGS

Further advantages and embodiments are evident from the accompanying drawings. In the drawings

FIG. 2 is a side view of an apparatus according to the invention;

FIG. 3 is a detailed view of an apparatus according to the invention, and

FIG. 4 is a detailed view of an apparatus according to the invention in a further embodiment.

DETAILED DESCRIPTION OF THE INVENTION

Figure 1A:
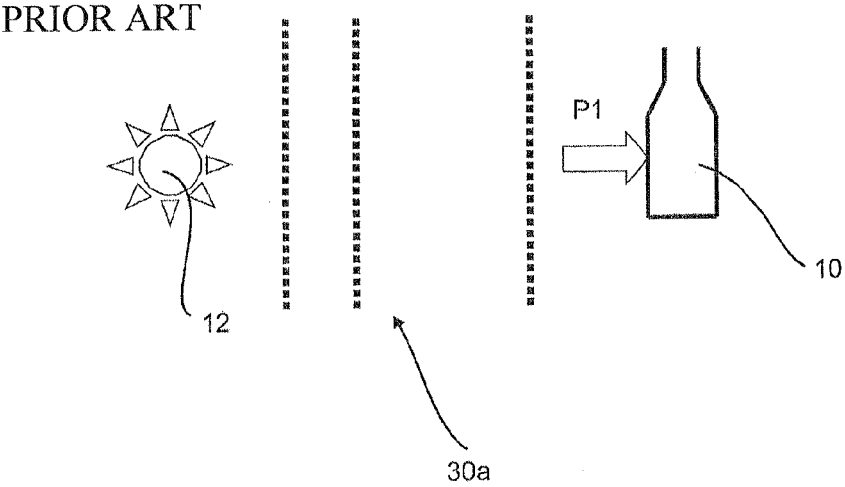
FIGS. 1a, 1b are two diagrammatic illustrations to explain the problem underlying the invention.
Figure 1B:
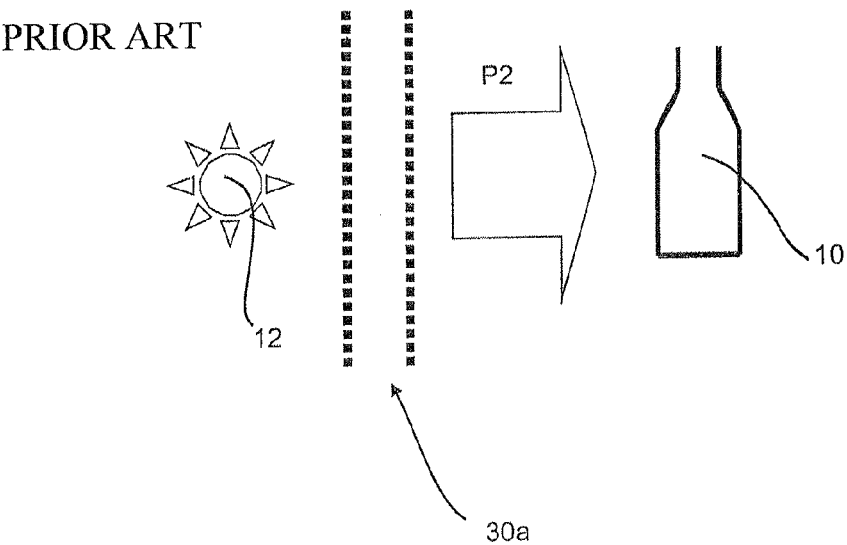

FIGS. 1a and 1b are two illustrations to explain the problem underlying the invention. In this case a charge carrier generation device is shown 12, which generates charge carriers. A plurality of barriers 30a, which are illustrated here by dotted lines, are present between this charge carrier generation device 12 and the container 10. By way of example, an outlet window of a sterilization device, air etc. can thus constitute a barrier of this type. In this way, one of the main drawbacks of previous plants and apparatus for the generation of electron beams is the problem of conveying the electrons from the generator source to the site of operation. The molecules which are present in the interspace and which occur in the air or in the existing outlet window, obstruct the reach of the electron beams to a significant degree.

As a consequence of this, the acceleration of the electrons has to be adapted, a step which in turn increases the size, the complexity, the risk potential, the screening and the costs of the plant as a whole.

In order not to have to implement these adverse factors for a further electron reach and nevertheless to carry out an adequate sterilization, it is proposed that steps should be taken so that the electrons required are conveyed at a smaller distance from the charge carrier generation source to the site of operation. This is illustrated in FIG. 1b. In this case the barriers 30a are reduced, so that as a result the electrons have a greater path to run. The larger arrow P2 as compared with the arrow P1 illustrates diagrammatically here the larger number of electrons which arrive at the container 10 or, expressed more precisely, at the inner wall thereof.

FIG. 2 is a diagrammatic illustration of an apparatus 1 according to the invention. In this case a carrier 8 is provided, which is rotatable about an axle or by means of a shaft 18 and on which a plurality of treatment stations or sterilization devices 2 are present.

In this case the respective containers 10 can be transferred to the apparatus 1 by means of a gripping device, it being advantageous for this gripping device to grip the plastics material containers from the outside and, in particular, below the carrying rings. After that, the containers are fixed by means of a holding device. Expressed more precisely, at each station or sterilization device 2 respectively the container or the plastics material pre-form can be directed into a suitably shaped docking region by way of an external gripper of a conveying star wheel. The reference number 26 designates diagrammatically a lifting device which for example brings a plastics material pre-form to the carrier 8 in such a way that the electron generation device arrives in the interior of plastics material container. It is thus advantageous for the plastics material container to be moved or turned over in the middle.

The surface of the neck of the plastics material pre-form is in contact in this case with a docking region. At the beginning of setting an under-pressure the external gripper of the transfer star wheel can still hold the plastics material container and at an adequate under-pressure (for example 800 mbar or less) it can release the plastics material container on the external gripper of the supply star wheel. The plastics material container obtained in this way is then irradiated by switching on the charge carrier generation source.

After a treatment time dependent upon the size of the pre-form the irradiation procedure is discontinued. This can be carried out for example by switching off the radiation current and advantageously the subsequent introduction of ambient air. With or during the pressure equalization the plastics material container can again be gripped by an external gripper of a removal star wheel. In this case the plastics material container can also be pulled downwards again so chat the charge carrier generation device is not damaged.

An optional external disinfection can be carried out by additional beam emitters, such as for example a surface radiator, which is connected in front of or after the internal treatment means. In addition, an external irradiation of the plastics material containers during the internal disinfection would also be possible.

Activation of the sterilization system, i.e. the charge carrier generation device, can start in this case before or after the generation of the under-pressure.

FIG. 3 shows an embodiment of an apparatus according to the invention. In this case too the charge carrier generation device 12 is again provided, which is used for the sterilization of the inside of the container. The reference number 16 relates to the holding device on which the container 10 is positioned by under-pressure. The reference number 20 relates to a pressure application device which in this case generates a vacuum in the interior of the plastics material container 10, in order to fasten the latter to the holding device 16 in this way. A major advantage of the apparatus according to the invention arises as a result of the process as proposed here which requires comparatively little effort and is comparatively simple. The stray radiation which occurs is minimal and the energy expenditure is also low. The reference number 10a relates to an inner wall of the plastics material container 10 and the reference 10b relates to an opening or mouth in the plastics material container 10.

The reference number 32 designates an optional electron conduction device which moves the electrons in the direction of the inner wall of the plastics material pre-forms. This electron conduction device can be designed in this case in the form of a sleeve which is acted upon with positive charge. In addition, it would be possible for the electron conduction device, as indicated by the broken line 34, to be situated in only one region of the plastics material pre-forms and for the plastics material pre-forms to be additionally rotated about their longitudinal direction L.

It was possible to establish that not only is an adequate sterilization of the containers possible by highly accelerated charge carriers, but it can be sufficient if the charge carriers arrive at the (inner) surface of the plastics material pre-forms or containers 10 respectively. The reference letter L designates the longitudinal direction of the containers 10.

FIG. 4 shows a further embodiment of an apparatus according to the invention. As well as the electrical conductor 22, which is also present in the case of the embodiment in FIG. 3, a further conductor 24 is provided here which acts as a replacement emitter here. This replacement emitter can be provided in this case parallel to or offset with respect to the conductor 22. In this case, if a control device ascertains damage to the first conductor 22, the second conductor 24 can be activated in order to generate the charge carriers in this way.

In contrast to the apparatus from the prior art, a complicated electron acceleration device and also a transfer path between the radiator outlet and the container inlet are dispensed with here. In this way, a major difference lies in the fact that in the proposed invention an electron cloud is used for sterilization purposes with acceleration voltage not present or with only minimal acceleration voltage. A number of advantages arise in this way. In the first place, the previous acceleration voltage is dispensed with, as a result of which there is a saving in energy. In addition, the kinetic energy of the effect in electrons is reduced and so a reduction in the X-ray radiation which occurs is achieved. In addition, a high-voltage generator required for the generation of the acceleration voltage can be dispensed with, and the necessary screening thickness can also be reduced and the plant can be simplified in its entirety, in which case a reduction in costs is also possible.

It is thus preferable for an electron cloud, which is conveyed to the surrounding surface of the container with or without a significantly reduced acceleration voltage, to be generated in a fine vacuum.

The Applicants reserve the right to claim all the features disclosed in the application documents as being essential to the invention, insofar as they are novel either individually or in combination as compared with the prior art.

LIST OF REFERENCES 1 apparatus
2 sterilization device
8 carrier
10 container
10a inner wall
10b opening in the container
12 charge carrier generation device
16 holding device
18 shaft
22 electrical conductor
24 further electrical conductor
26 lifting device
30a barriers
32, 34 electron conduction device
L longitudinal direction
P1, P2 arrow

The invention claimed is:

1. In the production of a container, a method of sterilizing an inner wall of the container by action of charge carriers, which comprises introducing a charge carrier generation device, comprising an electrical conductor, having an acceleration voltage below 100 kV by flowing a current through the conductor, directly into a plastic material pre-form for the container through an opening in the plastic material pre-form, and generating charge carriers in an interior of the plastic material pre-form, wherein an under-pressure of between 0.0001 mbar and 800 mbar, is generated inside the plastic material pre-form at least for a time before or during the sterilization procedure, providing an electron conduction device, in the form of a sleeve which is acted upon with positive charge, to direct the charge carriers in a direction of the inner wall of the plastic material pre-form, said sleeve surrounding the plastics material pre-form both on its sidewall and also on its bottom region.

2. The method according to claim 1, wherein the plastic material pre-form is conveyed along a pre-set conveying path during sterilization.

3. The method according to claim 1, wherein the plastics material pre-form is held on a holding device by an under-pressure.

4. The method according to claim 1, wherein the under-pressure is between 0.0003 mbar and 600 mbar.

5. The method according to claim 4, wherein the under-pressure is between 0.001 mbar and 300 mbar.

6. The method according to claim 1, wherein the charge carriers are electrons.

7. The method according to claim 1, wherein during the sterilization the plastic material pre-form is turned about a longitudinal axis with respect to the charge carrier generation device.

8. The method according to claim 7, wherein the charge carriers are accelerated in a predefined direction starting from the charge carrier generation device.

9. The method according to claim 1, wherein the charge carrier generation device has a first electrical conductor which is introduced into the plastic material pre-form and has a current flow through it.

10. The method according to claim 1, wherein the charge carrier generation device comprises a hot cathode.

11. The method according to claim 10, wherein the charge carrier generation device comprises a tungsten cathode.

12. The method according to claim 1, wherein sterilizing treatment time depends upon the size of the plastic material pre-form.

13. The method according to claim 1, wherein an electron conduction device, which is in the form of a sleeve which is acted upon with positive charge, is provided to direct the charge carriers in the direction of the inner wall of the plastic material pre-form.

14. The method according to claim 1, wherein the plastic material pre-form is rotated about its longitudinal axis, and an electron conduction device, which is acted upon with positive charge, is provided and situated in only one region of the plastic material pre-form to direct the charge carriers in the direction of the inner wall of the plastic material pre-form as the plastic material pre-form rotates about its longitudinal axis.

15. The method according to claim 9, wherein the charge carrier generation device has a second electrical conductor which is introduced into the container and has a current flow through it, which is connected parallel to the first electrical conductor and wherein the second electrical conductor is activated in the event of failure of the first electrical conductor.

16. The method according to claim 1, wherein an under-pressure, which is between 0.005 mbar and 600 mbar, is generated in the interior of the plastic material pre-form.

17. The method according to claim 1, wherein an under-pressure, which is between 0.001 mbar and 100 mbar, is generated in the interior of the plastic material pre-form.

18. The method according to claim 1, wherein the charge carriers have an acceleration voltage below 100 kV.

19. The method according to claim 1, wherein the charge carriers have an acceleration voltage below 50 kV.

20. The method according to claim 1, wherein the electrical conductor is introduced directly into the plastic material pre-form without a flask surrounding, and the under-pressure is generated in the plastic material itself.

21. The method according to claim 1, wherein the plastic material pre-form is held on a holding device by the under-pressure.

22. In the production of a container formed of plastic material, a method of sterilizing an inner wall of the container by action of charger carriers, which comprises introducing a charge carrier generation device directly into a plastic material pre-form for the container through an opening in the plastic material pre-form, and generating charge carriers having an acceleration voltage below 100 kV in an interior of the plastic material pre-form, wherein an under-pressure between 0.001 mbar and 800 mbar is generated inside the container at least for a time before or during the sterilization process, providing an electron conduction device, in the form of a sleeve which is acted upon with positive charge, to direct the charge carriers in a direction of the inner wall of the plastic material pre-form, said sleeve surrounding the plastics material pre-form both on its sidewall and also on its bottom region.

23. The method according to claim 22, wherein an under-pressure, which is between 0.003 mbar and 600 mbar is generated in the interior of the container.

24. The method according to claim 22, wherein an under-pressure, which is between 0.001 mbar and 300 mbar is generated in the interior of the container.

25. In the production of a container formed of plastic material, a method of sterilizing an inner wall of the container by action of charger carriers, which comprises introducing a charge carrier generation device directly into a plastic material pre-form for the container through an opening in the plastic material pre-form, and generating charge carriers having an acceleration voltage below 100 kV in an interior of the plastic material pre-form, and drawing an under-pressure between 0.001 mbar and 600 mbar inside the container at least for a time before or during the sterilization process, providing an electron conduction device, in the form of a sleeve which is acted upon with positive charge, to direct the charge carriers in a direction of the inner wall of the plastic material pre-form said sleeve surrounding the plastics material pre-form both on its sidewall and also on its bottom region.

26. The method according to claim 25, wherein an under-pressure of between 0.001 mbar and 300 mbar drawing in the interior of the container.

* * * * *

UNITED STATES PATENT AND TRADEMARK OFFICE
CERTIFICATE OF CORRECTION

PATENT NO.       : 9,078,935 B2
APPLICATION NO.  : 13/625864
DATED            : July 14, 2015
INVENTOR(S)      : Knott et al.

It is certified that error appears in the above-identified patent and that said Letters Patent is hereby corrected as shown below:

In the claims

Claim 25, Col. 10, line 14, "pre-form said" should be --pre-form, said--.

Signed and Sealed this
Fifteenth Day of December, 2015

Michelle K. Lee
*Director of the United States Patent and Trademark Office*